United States Patent
Teng et al.

(10) Patent No.: US 10,605,663 B2
(45) Date of Patent: Mar. 31, 2020

(54) FOURIER DOMAIN DYNAMIC CORRECTION METHOD FOR COMPLEX OPTICAL FRINGES IN LASER SPECTROMETERS

(71) Applicants: INTERNATIONAL BUSINESS MACHINES CORPORATION, Armonk, NY (US); The Trustees of Princeton University, Princeton, NJ (US)

(72) Inventors: Cheyenne Teng, Princeton, NJ (US); Gerard Wysocki, Princeton, NJ (US); Eric J. Zhang, Yonkers, NY (US); William M. Green, Irvington, NY (US)

(73) Assignees: INTERNATIONAL BUSINESS MACHINES CORPORATION, Armonk, NY (US); THE TRUSTEES OF PRINCETON UNIVERSITY, Princeton, NJ (US)

( * ) Notice: Subject to any disclaimer, the term of this patent is extended or adjusted under 35 U.S.C. 154(b) by 25 days.

(21) Appl. No.: 15/981,467

(22) Filed: May 16, 2018

(65) Prior Publication Data

US 2019/0353525 A1 Nov. 21, 2019
US 2020/0064192 A9 Feb. 27, 2020

Related U.S. Application Data

(60) Provisional application No. 62/598,089, filed on Dec. 13, 2017.

(51) Int. Cl.
*G01J 3/453* (2006.01)
*G01N 21/3504* (2014.01)
(Continued)

(52) U.S. Cl.
CPC .............. *G01J 3/453* (2013.01); *G01J 3/4338* (2013.01); *G01N 21/3504* (2013.01); *G01J 2003/423* (2013.01)

(58) Field of Classification Search
CPC .... G01J 3/453; G01J 3/4338; G01J 2003/423; G01N 21/3504
See application file for complete search history.

(56) References Cited

U.S. PATENT DOCUMENTS 5,146,414 A * 9/1992 McKown ............... A61B 5/026
600/526
5,838,438 A 11/1998 Peale et al.
(Continued)

OTHER PUBLICATIONS

Faggin, Marc F., and Melissa A. Hines. "Improved algorithm for the suppression of interference fringe in absorption spectroscopy." Review of scientific instruments 75.11 (2004): 4547-4553 (Year: 2004).*

(Continued)

*Primary Examiner* — Dominic J Bologna
(74) *Attorney, Agent, or Firm* — Tutunjian & Bitetto, P.C.; Vazken Alexanian (57) ABSTRACT

A method is provided for Fourier domain dynamic correction of optical fringes in a laser spectrometer. The method includes Fourier transforming a background spectrum contaminated with the optical fringes to obtain baseline fringes in a frequency domain. The method includes partitioning the baseline fringes in the frequency domain using bandpass filtering to obtain partitioned baseline fringes. The method includes reconstructing the partitioned baseline fringes as separate spectra using an inverse Fourier transform. The method includes constructing a fitting model to approximate the background spectrum by assigning a first and a second free parameter to each of partitioned baseline fringe components to respectively allow for drift and amplitude adjustments during a fitting of the fitting model. The method includes applying the fitting model to a newly acquired spectrum to provide an interpretation of the newly acquired spectrum having a reduced influence of spectral contamination on concentration retrieval.

20 Claims, 9 Drawing Sheets

(51) Int. Cl.
 *G01J 3/433* (2006.01)
 *G01J 3/42* (2006.01)

(56) References Cited

U.S. PATENT DOCUMENTS

| | | |
|---|---|---|
| 6,584,413 B1 | 6/2003 | Keenan et al. |
| 6,687,620 B1 | 2/2004 | Haaland et al. |
| 6,983,213 B2 | 1/2006 | Wang |
| 7,072,772 B2 | 7/2006 | Ahmed et al. |
| 7,230,711 B1 | 6/2007 | Hovde |
| 8,970,842 B2 | 3/2015 | Sun et al. |
| 9,645,077 B2 | 5/2017 | Ognibene et al. |
| 9,651,488 B2 | 5/2017 | Scherer et al. |
| 9,976,903 B2 * | 5/2018 | Oto .................. G01J 3/0224 |
| 10,082,457 B2 * | 9/2018 | Green ................ G01N 21/27 |
| 2007/0081162 A1 | 4/2007 | Roller et al. |
| 2010/0211329 A1 * | 8/2010 | Farquharson ...... G01N 21/359 702/28 |

OTHER PUBLICATIONS

Bomse et al., An adaptive singular value decomposition (SVD) algorithm for analysis of wavelength modulation spectra, Appl. Phys., Jun. 2006, B 85, 461-466 (2006), 6 pages.

Ehlers et al., "Use of etalon-immune distances to reduce the influence of background signals in frequency-modulation spectroscopy and noise-immune cavityenhanced optical heterodyne molecular spectroscopy", J. Opt. Soc. Am. B / vol. 31, No. 12 / Dec. 2014, pp. 2938-2945.

Hjelme et al., "Optical interference fringe reduction in frequency-modulation spectroscopy experiments", Optics Letters, Aug. 15, 1995 / vol. 20, No. 16, pp. 1731-1733.

Silver et al., "Optical interterence fringe reduction in laser absorption experiments", Applied Optics / May 15, 1988/ vol. 27, No. 10 /, pp. 1914-1916.

Teng et al., "Fiber-pigtailed silicon photonic sensors for methane leak detection", CLEO 2017, May 2017, 2 pages.

Tombez et al., "Methane absorption spectroscopy on a silicon photonic chip", Optica, Nov. 2017, vol. 4, No. 11, pp. 1322-1325.

Werle, P., "Accuracy and precision of laser spectrometers for trace gas sensing in the presence of optical fringes and atmospheric turbulence", Appl Phys B, Aug. 2011, 102: 313-329, pp. 313-328.

Zhang et al., "Silicon photonic on-chip trace-gas spectroscopy of methane", CLEO 2016, Mar. 2016, 2 pages.

* cited by examiner

FOURIER DOMAIN DYNAMIC CORRECTION METHOD FOR COMPLEX OPTICAL FRINGES IN LASER SPECTROMETERS

STATEMENT REGARDING FEDERALLY SPONSORED RESEARCH OR DEVELOPMENT

This invention was made with Government support under Contract Number DE-AR0000540 awarded by the U.S. Dept. of Energy. The Government has certain rights in this invention.

BACKGROUND

Technical Field

The present invention generally relates to optical devices, and more particularly to a Fourier domain dynamic correction method for complex optical fringes in laser spectrometers.

Description of the Related Art

Optical interference effects produce fringe noise which is present in most spectroscopic systems that utilize coherent laser sources. Over the past decades, there have been many approaches to suppress this fringe noise. However, since the fringes can change in time due to external effects (e.g., changes in temperature, pressure, and so forth), the fringes can be misinterpreted by spectral fitting routines as the useful spectral signature of the target analyte, which causes unwanted drift in spectroscopic sensing systems. Accordingly, there is a need for an improved correction method for complex optical fringes in laser spectrometers.

SUMMARY

According to an aspect of the present invention, a computer-implemented method is provided for Fourier domain dynamic correction of optical fringes in a laser spectrometer. The method includes Fourier transforming, by a processor, a background spectrum contaminated with the optical fringes to obtain baseline fringes in a frequency domain. The method further includes partitioning, by the processor, the baseline fringes in the frequency domain using bandpass filtering to obtain partitioned baseline fringes. The method also includes reconstructing, by the processor, the partitioned baseline fringes as separate spectra using an inverse Fourier transform. The method additionally includes constructing, by the processor, a fitting model to approximate the background spectrum by assigning a first and a second free parameter to each of partitioned baseline fringe components to respectively allow for drift and amplitude adjustments during a fitting of the fitting model. The method further includes applying, by the processor, the fitting model to a newly acquired spectrum to provide an interpretation of the newly acquired spectrum having a reduced influence of spectral contamination on concentration retrieval.

According to another aspect of the present invention, a computer program product is provided for Fourier domain dynamic correction of optical fringes in a laser spectrometer. The computer program product includes a non-transitory computer readable storage medium having program instructions embodied therewith. The program instructions are executable by a computer to cause the computer to perform a method. The method includes Fourier transforming, by a processor, a background spectrum contaminated with the optical fringes to obtain baseline fringes in a frequency domain. The method further includes partitioning, by the processor, the baseline fringes in the frequency domain using bandpass filtering to obtain partitioned baseline fringes. The method also includes reconstructing, by the processor, the partitioned baseline fringes as separate spectra using an inverse Fourier transform. The method additionally includes constructing, by the processor, a fitting model to approximate the background spectrum by assigning a first and a second free parameter to each of partitioned baseline fringe components to respectively allow for drift and amplitude adjustments during a fitting of the fitting model. The method further includes applying, by the processor, the fitting model to a newly acquired spectrum to provide an interpretation of the newly acquired spectrum having a reduced influence of spectral contamination on concentration retrieval.

According to yet another aspect of the present invention, a system is provided for Fourier domain dynamic correction of optical fringes in a laser spectrometer. The system includes a memory for storing program code. The system further includes a processor, operatively coupled to the memory, for running the program code to Fourier transform a background spectrum contaminated with the optical fringes to obtain baseline fringes in a frequency domain. The processor further runs the program code to partition the baseline fringes in the frequency domain using bandpass filtering to obtain partitioned baseline fringes. The processor also runs the program code to reconstruct the partitioned baseline fringes as separate spectra using an inverse Fourier transform. The processor additionally runs the program code to construct a fitting model to approximate the background spectrum by assigning a first and a second free parameter to each of partitioned baseline fringe components to respectively allow for drift and amplitude adjustments during a fitting of the fitting model. The processor further runs the program code to apply the fitting model to a newly acquired spectrum to provide an interpretation of the newly acquired spectrum having a reduced influence of spectral contamination on concentration retrieval.

These and other features and advantages will become apparent from the following detailed description of illustrative embodiments thereof, which is to be read in connection with the accompanying drawings.

BRIEF DESCRIPTION OF THE DRAWINGS

The following description will provide details of preferred embodiments with reference to the following figures wherein.

DETAILED DESCRIPTION

The present invention is directed to a Fourier domain dynamic correction (removal) method for complex optical fringes in laser spectrometers.

In an embodiment, the present invention provides a novel method that improves concentration retrieval from a direct absorption spectrum contaminated by complex fringe noise.

In an embodiment, the present invention is designed to improve the stability of laser-based direct absorption spectroscopy systems affected by fringe noise. The novel features of the present invention are particularly useful for low-cost spectroscopy systems where it may not be possible to address fringes through meticulous system engineering that is often required to reduce optical fringing. As an example, the present invention is suitable for the integrated silicon photonic waveguide sensors that suffer from extensive fringe noise. Of course, the present invention can be applied to other types of sensors and systems, while maintaining the spirit of the present invention.

The present invention is designed to be capable of fringe suppression where other techniques may not be applicable or effective. For example, moving mechanical parts may not always be tolerated as a means to randomly dither fringes (such as in the case of integrated silicon photonic sensors). Many modulation techniques can target a specific fringe/fringes by carefully choosing the modulation frequency, but these techniques cannot address situations where multiple dominant fringes are present in the system. There have also been adaptive numerical approaches that can suppress slowly drifting fringes, which is not applicable to systems with large amplitude fringes that are not precisely thermally stabilized.

Advantageously, the present invention can be readily incorporated into any direct absorption gas sensing system, is suitable for fast-drifting fringes and complex fringe structures and can be easily adapted to existing direct absorption gas sensing systems without hardware modifications. These and other advantages of the present invention are readily determined by one of ordinary skill in the art, given the teachings of the present invention provided herein.

In an embodiment, the present invention uses the fact that the shapes of optical fringes are in fact well-constrained and so do not require multiple sets of measurements for characterization. A single spectral acquisition, followed by Fourier domain analysis, is sufficient to identify the "form" of the fringes, and the corresponding inverse Fourier transform is used to "model" the fringe background. In this way, changes in fringe patterns can be approximated and fringe correction can be achieved.

Figure 1:
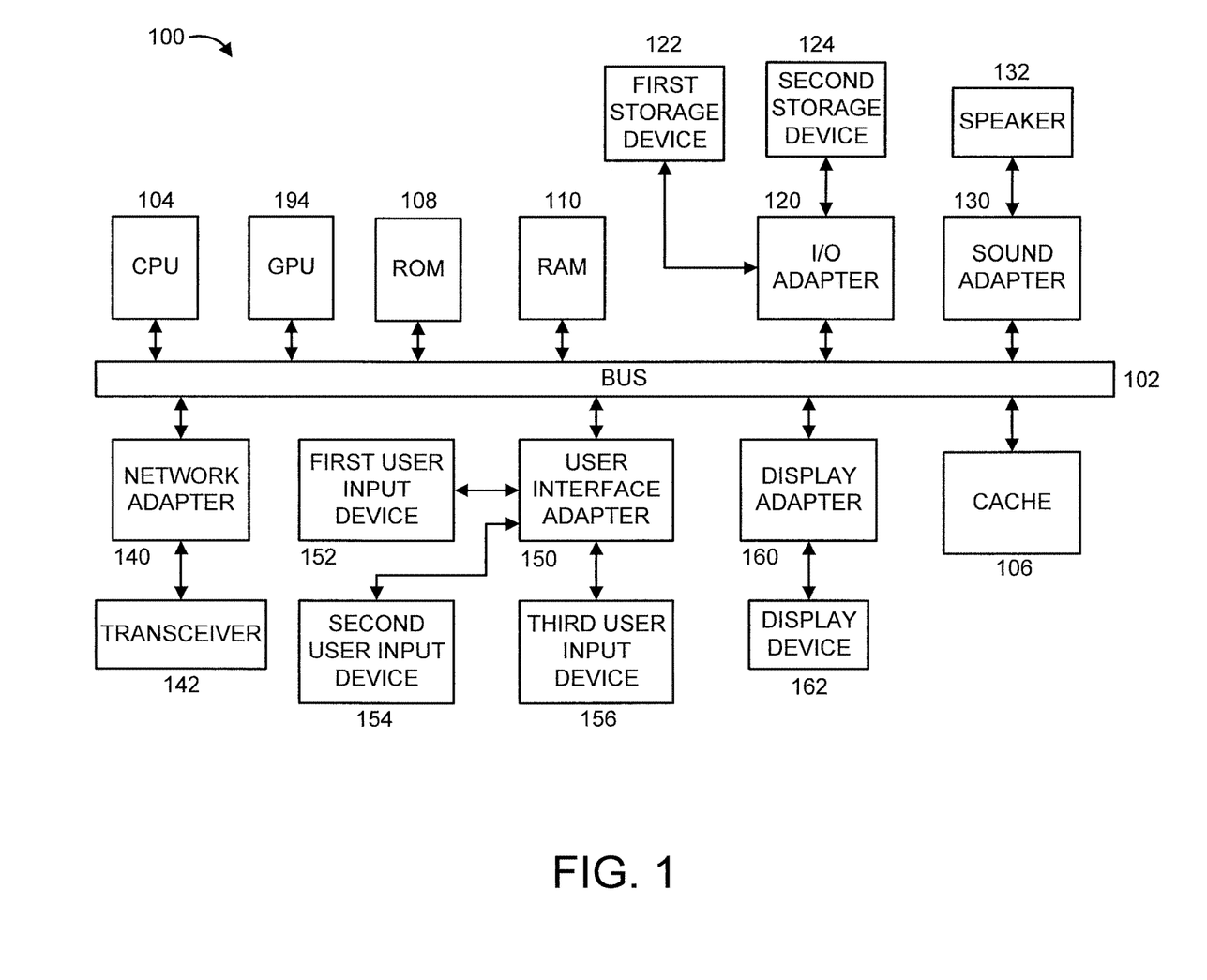
FIG. 1 is a block diagram showing an exemplary processing system to which the present invention may be applied, in accordance with an embodiment of the present invention.

FIG. 1 is a block diagram showing an exemplary processing system 100 to which the present invention may be applied, in accordance with an embodiment of the present invention. The processing system 100 is coupled to, or part of, a laser spectrometer. The processing system 100 includes program code to enable the processing system 100 to perform Fourier domain dynamic correction for optical fringes in the laser spectrometer. While processing system 100 is shown here for the sake of illustration, other configurations of processing systems can also be used in accordance with the teachings of the present invention, while maintaining the spirit of the present invention.

The processing system 100 includes at least one processor (CPU) 104 operatively coupled to other components via a system bus 102. A cache 106, a Read Only Memory (ROM) 108, a Random Access Memory (RAM) 110, an input/output (I/O) adapter 120, a sound adapter 130, a network adapter 140, a user interface adapter 150, and a display adapter 160, are operatively coupled to the system bus 102. At least one Graphics Processing Unit (GPU) 194 is operatively coupled to the system bus 102.

A first storage device 122 and a second storage device 124 are operatively coupled to system bus 102 by the I/O adapter 120. The storage devices 122 and 124 can be any of a disk storage device (e.g., a magnetic or optical disk storage device), a solid state magnetic device, and so forth. The storage devices 122 and 124 can be the same type of storage device or different types of storage devices.

A speaker 132 is operatively coupled to system bus 102 by the sound adapter 130. A transceiver 142 is operatively coupled to system bus 102 by network adapter 140. A display device 162 is operatively coupled to system bus 102 by display adapter 160.

A first user input device 152, a second user input device 154, and a third user input device 156 are operatively coupled to system bus 102 by user interface adapter 150. The user input devices 152, 154, and 156 can be any of a keyboard, a mouse, a keypad, an image capture device, a motion sensing device, a microphone, a device incorporating the functionality of at least two of the preceding devices, and so forth. Of course, other types of input devices can also be used, while maintaining the spirit of the present invention. The user input devices 152, 154, and 156 can be the same type of user input device or different types of user input devices. The user input devices 152, 154, and 156 are used to input and output information to and from system 100.

Of course, the processing system 100 may also include other elements (not shown), as readily contemplated by one of skill in the art, as well as omit certain elements. For example, various other input devices and/or output devices can be included in processing system 100, depending upon the particular implementation of the same, as readily understood by one of ordinary skill in the art. For example, various types of wireless and/or wired input and/or output devices can be used. Moreover, additional processors, controllers, memories, and so forth, in various configurations can also be utilized as readily appreciated by one of ordinary skill in the art. These and other variations of the processing system 100 are readily contemplated by one of ordinary skill in the art given the teachings of the present invention provided herein.

Figure 2:
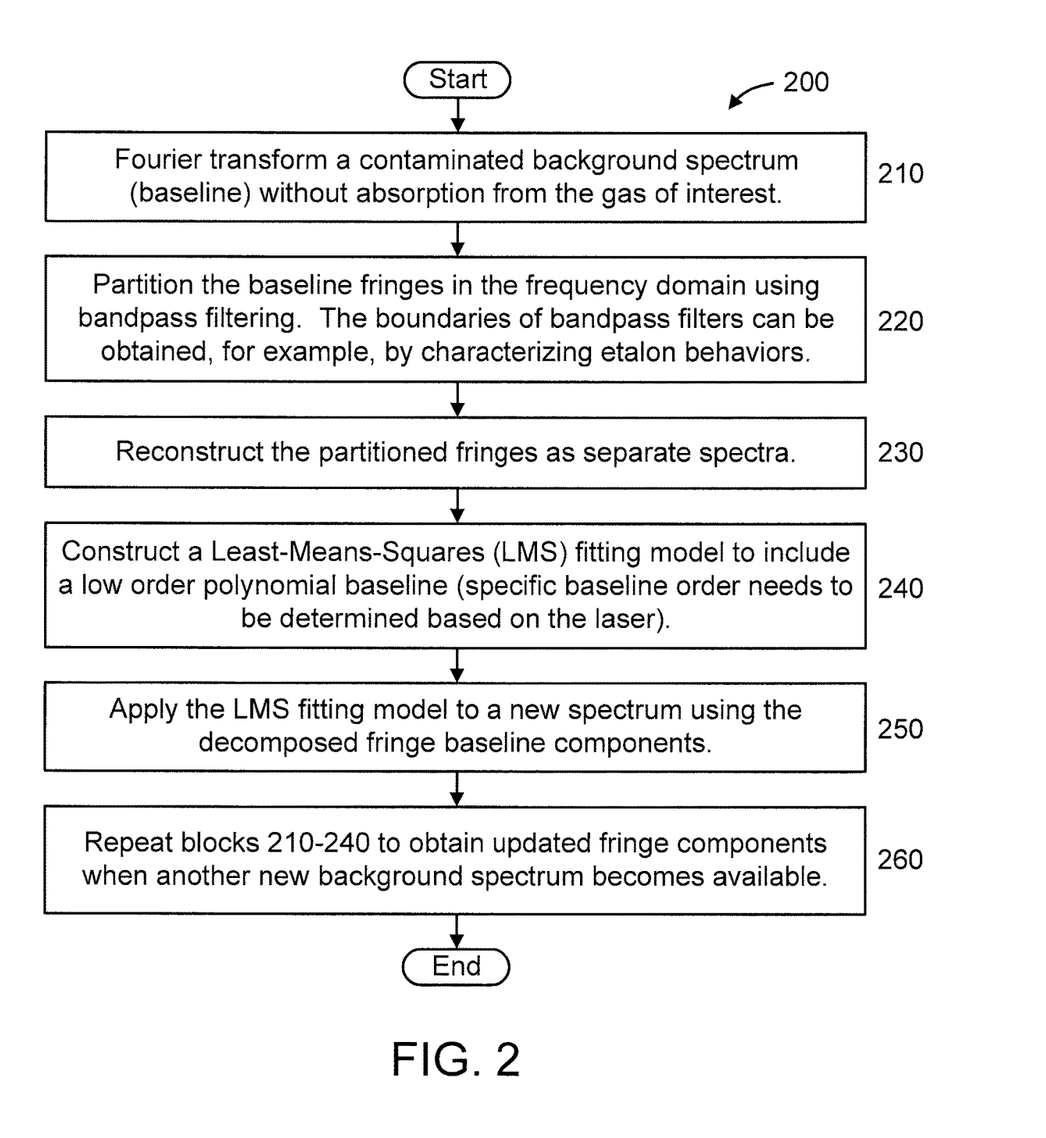
FIG. 2 is a flow diagram showing an exemplary method for Fourier Transform dynamic correction for optical fringes in laser spectrometers, in accordance with an embodiment of the present invention.

Moreover, it is to be appreciated that processing system 100 may perform at least part of the method described herein including, for example, at least part of method 200 of FIG. 2.

The present invention is a methodology to be applied during concentration retrieval from an absorption spectrum. The absorption spectrum can be obtained as usual by scanning the laser frequency across the absorption profile of a gas. According to the Beer-Lambert Law, the amount of attenuation of incident light is related to the concentration of the gas in the optical path, and the present invention is used to distinguish this signal from unwanted spectral features due to fringes.

FIG. 2 is a flow diagram showing an exemplary method 200 for Fourier Transform dynamic correction for optical fringes in laser spectrometers, in accordance with an embodiment of the present invention.

Figure 3:
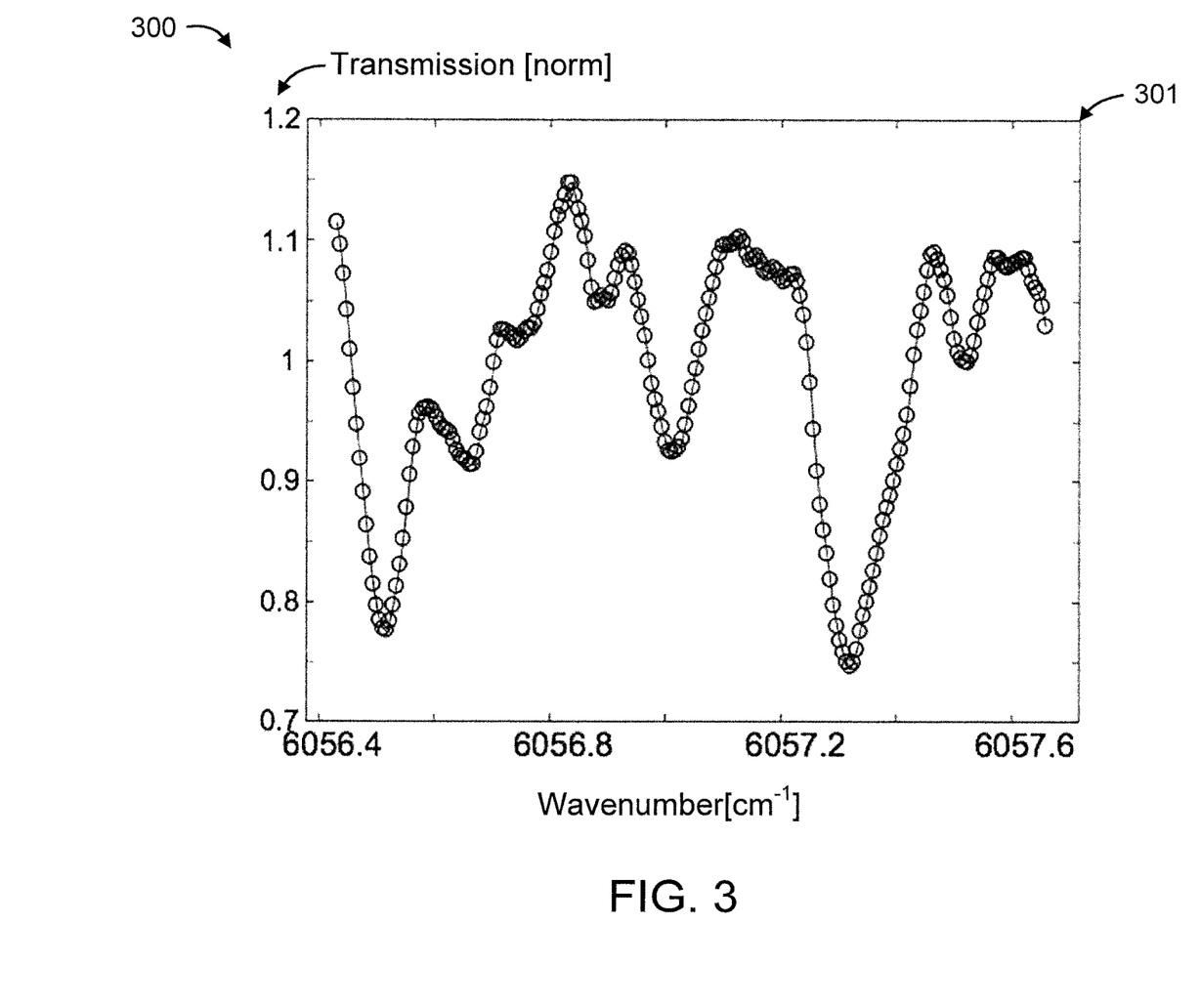
FIG. 3 is a plot showing a baseline-normalized zero gas background spectrum with prominent etalon features from a fiber-pigtailed Silicon photonic waveguide sensor, in accordance with an embodiment of the present invention.

At block 210, Fourier transform a contaminated background spectrum (baseline) without absorption from the gas of interest. As used herein, the phrase "contaminated background spectrum" refers to a background spectrum that suffers from one or more contaminants. The contaminants can be caused by and/or otherwise related to, for example, but are not limited to, changes in environmental conditions (e.g., but not limited to, temperature, pressure, humidity, and so forth), design and/or manufacturing defects in the laser spectrometer and/or related equipment, and/or so forth. FIG. 3 is a plot 301 showing a baseline-normalized zero gas background spectrum 300 with prominent etalon features from a fiber-pigtailed Silicon photonic waveguide sensor, in accordance with an embodiment of the present invention. The plot 301 shows wavenumber (in $cm^{-1}$) in the x-axis versus transmission (normalized) in the y-axis.

Figure 4:
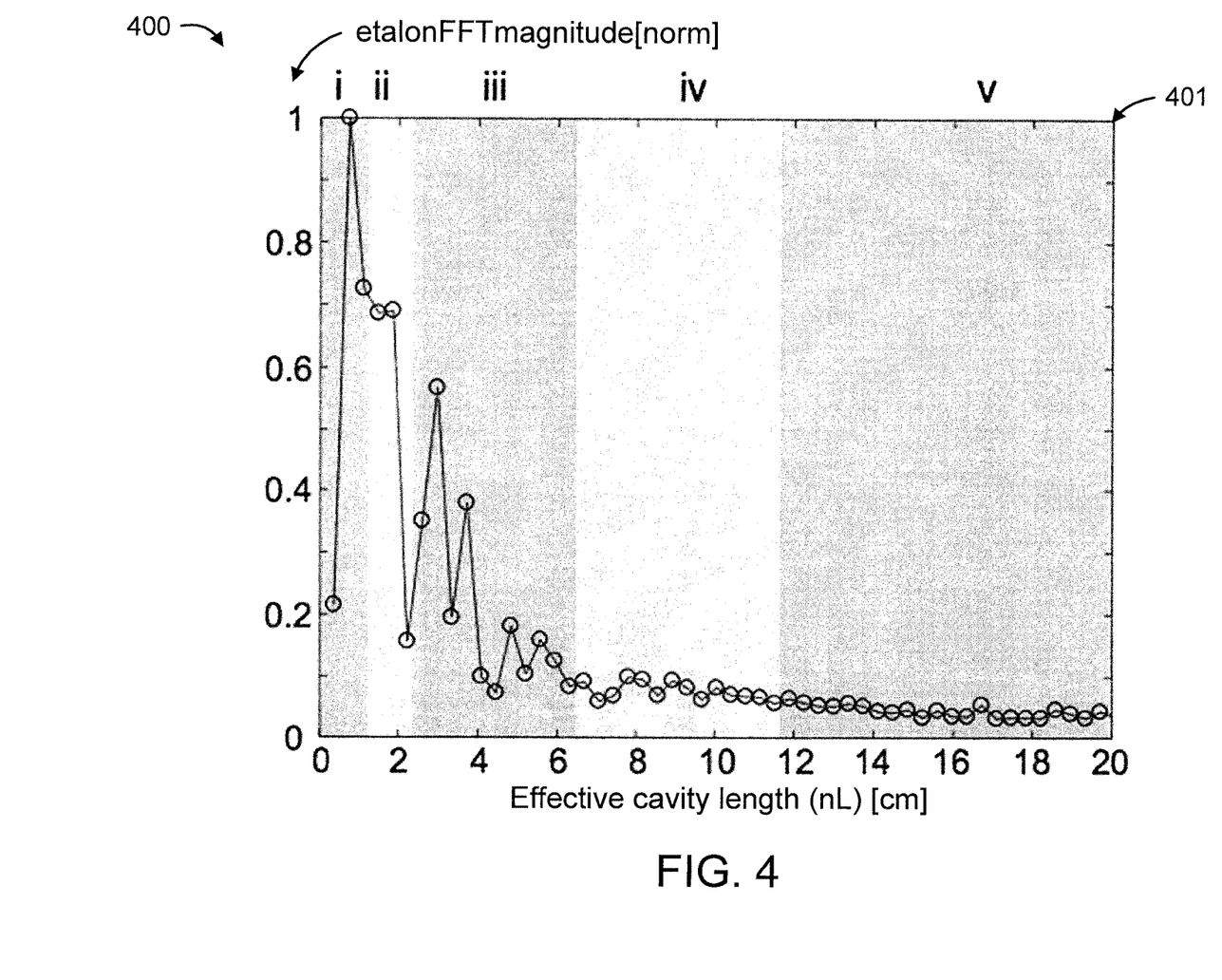
FIG. 4 is a plot showing a Fourier transform of the zero-gas spectrum and band-pass partitioning, in accordance with an embodiment of the present invention.

At block 220, partition the baseline fringes in the frequency domain using bandpass filtering. In an embodiment, etalons of different effective cavity lengths can move at different rates and therefore need to be separated prior to correction, which is achieved by bandpass filtering the Fourier transformed baseline fringes. The boundaries of bandpass filters can be obtained, for example, by characterizing the etalon behaviors. Such a characterization can be achieved by tracking the Fourier phase of etalons corresponding to different effective cavity lengths over some time duration during which etalon drift is observed. FIG. 4 is a plot 401 showing a Fourier transform of the zero-gas spectrum and band-pass partitioning 400, in accordance with an embodiment of the present invention. The plot 401 shows effective cavity length (in cm) in the (lower) x-axis versus etalon FFT magnitude (etalonFFTmagnitude) (normalized) in the y-axis. Moreover, the upper x-axis shows Roman numbers i through v, each representing a respective bandpass filter applied to the Fourier transform of the zero-gas spectrum to partition the baseline fringes.

Figure 5:
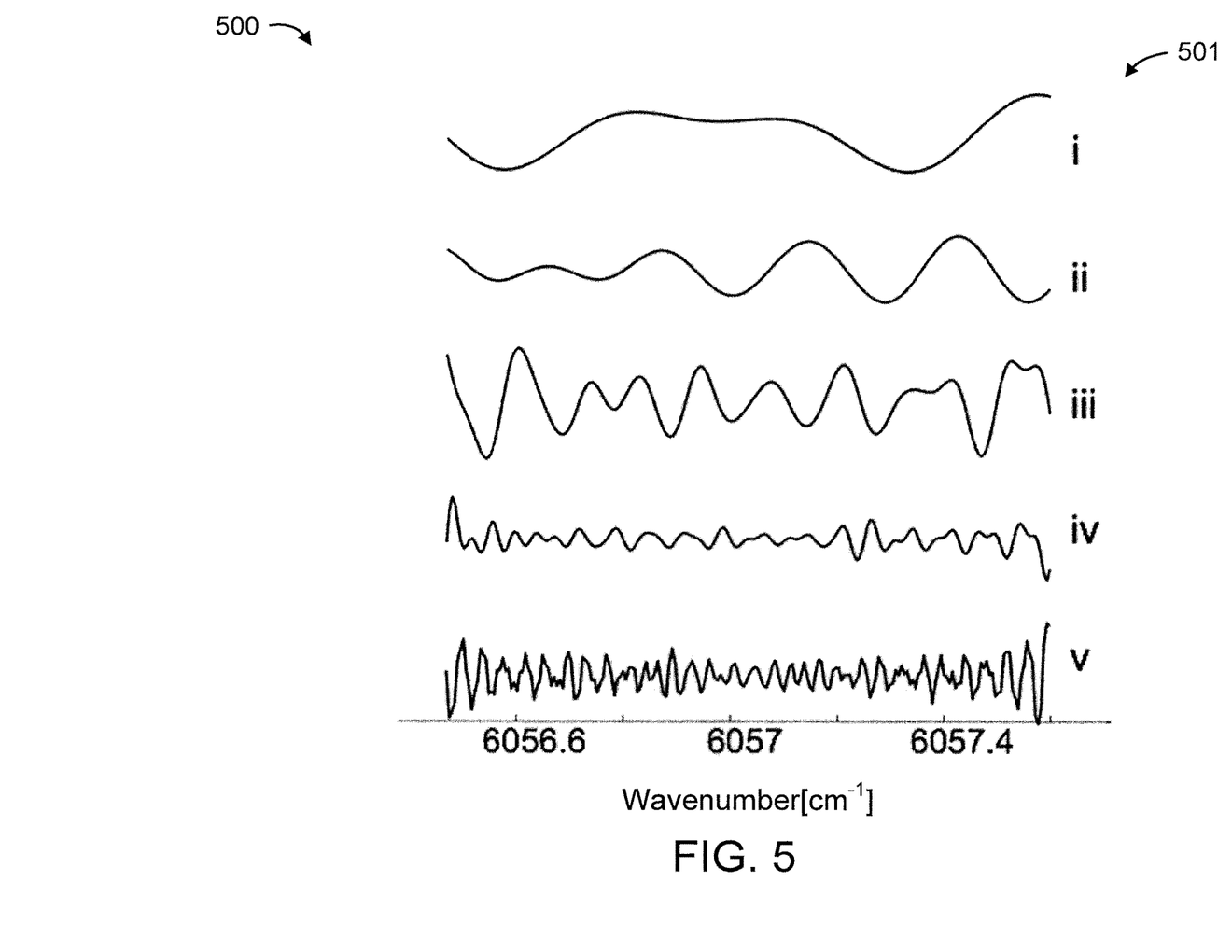
FIG. 5 is a plot showing a reconstruction of partitioned fringes corresponding to each of the labeled sections in FIG. 4, in accordance with an embodiment of the present invention.

At block 230, reconstruct the partitioned fringes as separate spectra. Each component (spectra) now includes etalons of a smaller range of effective cavity lengths. FIG. 5 is a plot 501 showing a reconstruction 500 of partitioned fringes corresponding to each of the labeled sections in FIG. 4, in accordance with an embodiment of the present invention. The plot 501 shows wavelength number (in $cm^{-1}$) in the x-axis versus each of the separate spectra in the y-axis. The separate spectra in plot 501 are labelled using the same Roman numbers (i through v) corresponding to the bandpass filtering of block 220.

At block 240, construct a Least-Means-Squares (LMS) fitting model to approximate the current background spectrum (which has changed from the initial background spectrum obtained in 210). In an embodiment, the background fringe pattern is reconstructed by summation of decomposed fringe spectra (shown in plot 501), each of which are assigned two free parameters (two degrees of freedom) to allow for drift and amplitude adjustments during LMS fitting. Of course, other numbers of degrees of freedom/ parameters can also be used, while maintaining the spirit of the present invention. In an embodiment, the resultant reconstruction can be considered to be an "intelligent" reconstruction based on multiple frequency groupings. In addition to the fringe background, the overall background spectrum also includes the effect of laser L-I characteristic, due to the fact that changing the laser frequency leads to changes in laser output power. A $2^{nd}$ or $3^{rd}$ order polynomial baseline is generally applicable to approximate the laser L-I characteristic, but specific baseline polynomial order needs to be determined based on the laser. For example, in an embodiment, the polynomial baseline order most suitable for a specific laser can be determined by measuring the direct laser output power (without elements that may cause fringes) as the laser frequency is scanned across the spectral region of interest. In an embodiment, the aggregate LMS fitting model includes the modeled gas absorption profile (linestrength and lineshape parameters of the gas molecule transition can be obtained from existing database such as the HITRAN database) and the approximated spectral background including the current fringe background and laser L-I behavior.

At block 250, apply the LMS fitting model to a new spectrum using the decomposed fringe baseline components. The application of the LMS fitting model to the new spectrum using the decomposed fringe baseline components allows for the interpretation of the new spectrum with optical fringe correction.

At block 260, repeat blocks 210-240 to obtain updated fringe components when another new background spectrum becomes available. These updated fringe components can then be used with the LMS fitting model to interpret the other new background spectrum using the updated fringe components to provide optical fringe correction.

It is to be appreciated that in cases of complicated interferences, the resulting Fourier transform may include overlapping etalons that cannot be effectively separated. For this reason, the partitioned etalon components are usually not valid permanently as varying behaviors of overlapping etalons cannot be addressed individually. This problem can be improved with careful selection of partitioning regions based on empirical observations. Finer partitioning can also be used to accommodate more complicated structures to minimize the effects of overlapping etalons.

The method 200 described herein with respect to FIG. 2 has been tested on a Silicon photonic waveguide sensor, which features a highly dynamic and complex fringe baseline.

The fringe corrected interpretation of a spectrum using method 200 can, in turn, be used for a myriad of uses, as readily appreciated by one of ordinary skill in the art. For example, some of the myriad of uses include, but are not limited to, determining the elemental composition of materials, monitoring dissolved oxygen content in freshwater and marine ecosystems, detecting petroleum hydrocarbons in groundwater and in soil, studying spectral emission lines of distant galaxies, characterizing proteins, space exploration, respiratory gas analysis in hospitals, diagnosing disease and extracting histochemical and histopathological information, and so forth. The preceding uses are merely illustrative.

Figure 6:
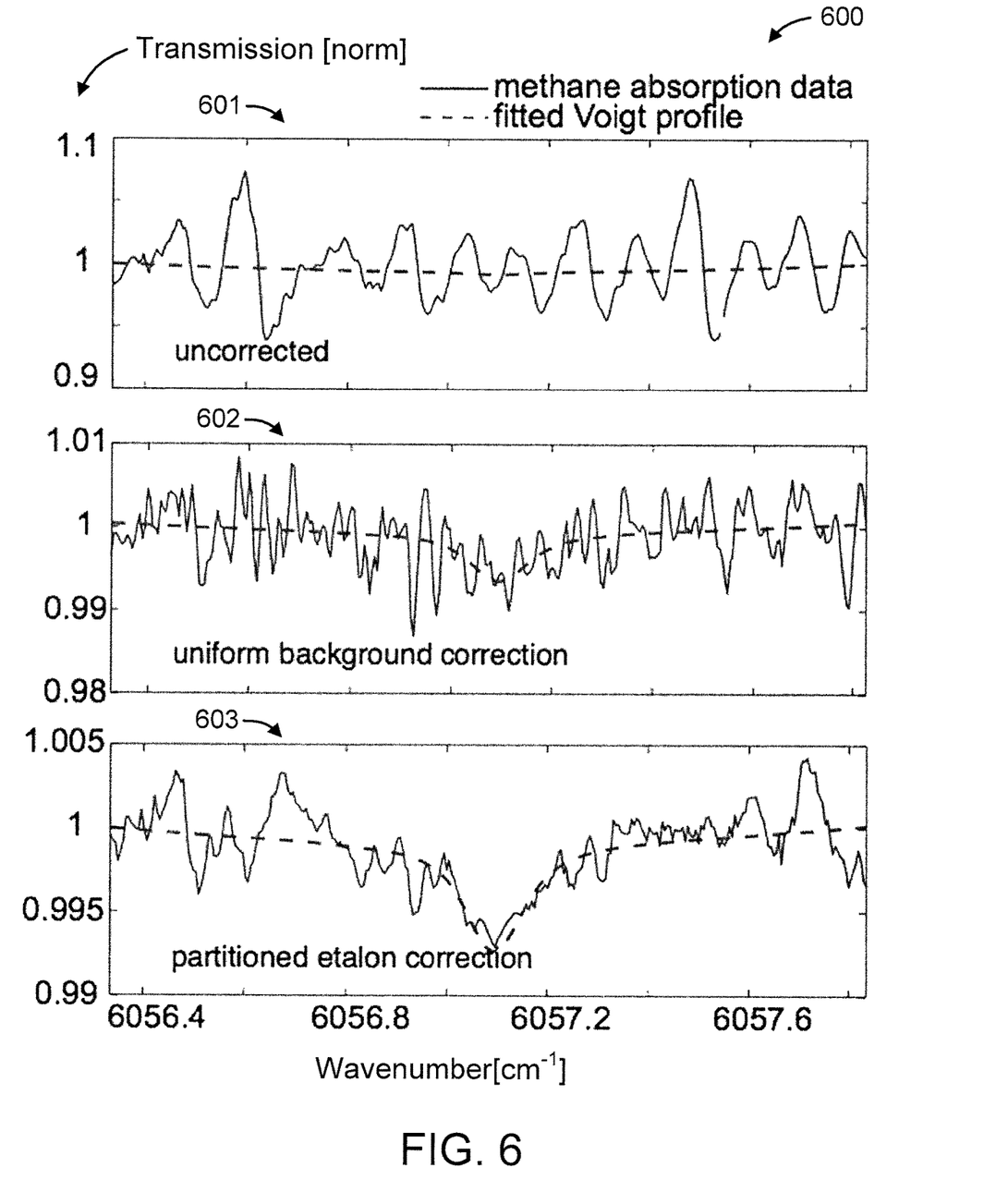
FIG. 6 is a diagram comparing three concentration retrieval methods that are applied on a methane absorption spectrum, in accordance with an embodiment of the present invention.

FIG. 6 is a diagram comparing three concentration retrieval methods (601, 602, and 603, respectively) that are applied on a methane absorption spectrum (30% methane with 2.5 cm effective path length), in accordance with an embodiment of the present invention. The concentration retrieval methods 601, 602, and 603 can be respectively considered as follows: uncorrected; uniform background correction; and partitioned etalon correction, respectively. For each of the retrieval methods 601, 602, and 603, the methane absorption data and the fitted Voigt profile are shown.

The first spectrum 611, resulting from the first concentration retrieval method 601, is a result of direct background subtraction without correction. Evidently the fringe background makes it difficult to extract any meaningful methane spectrum signal. In the second spectrum 612, resulting from the second concentration retrieval method 602, uniform background drift is allowed, and dramatic improvement of signal-to-fringe ratio is observed. In the third spectrum 613, corresponding to the third concentration retrieval method 603, we apply the procedure described in FIG. 2, and further improvement in signal-to-fringe ratio is shown.

Figure 7:
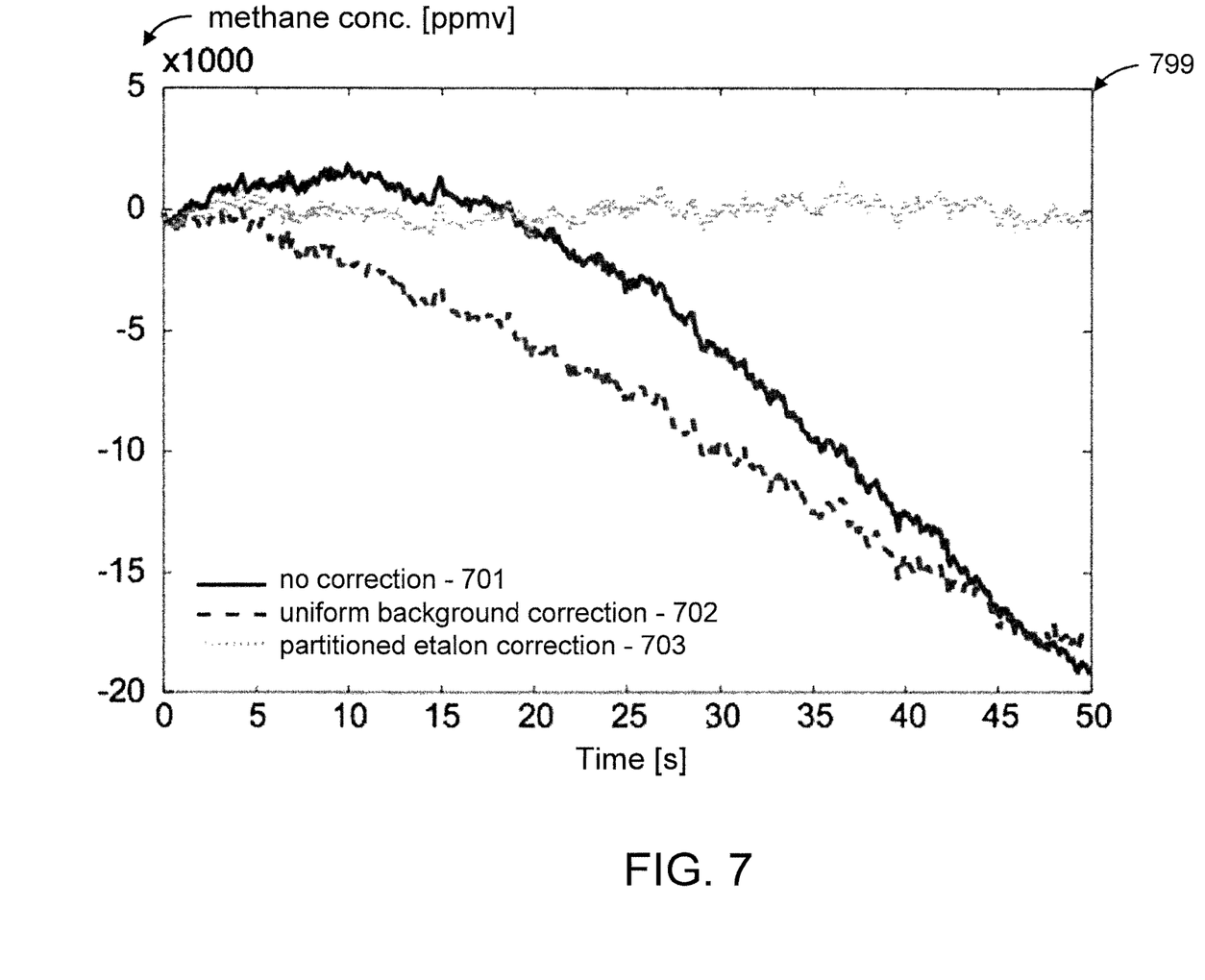
FIG. 7 is a plot showing a time series of three zero-gas measurements using the same silicon photonic waveguide sensor under the three different scenarios, in accordance with an embodiment of the present invention.
Figure 8:
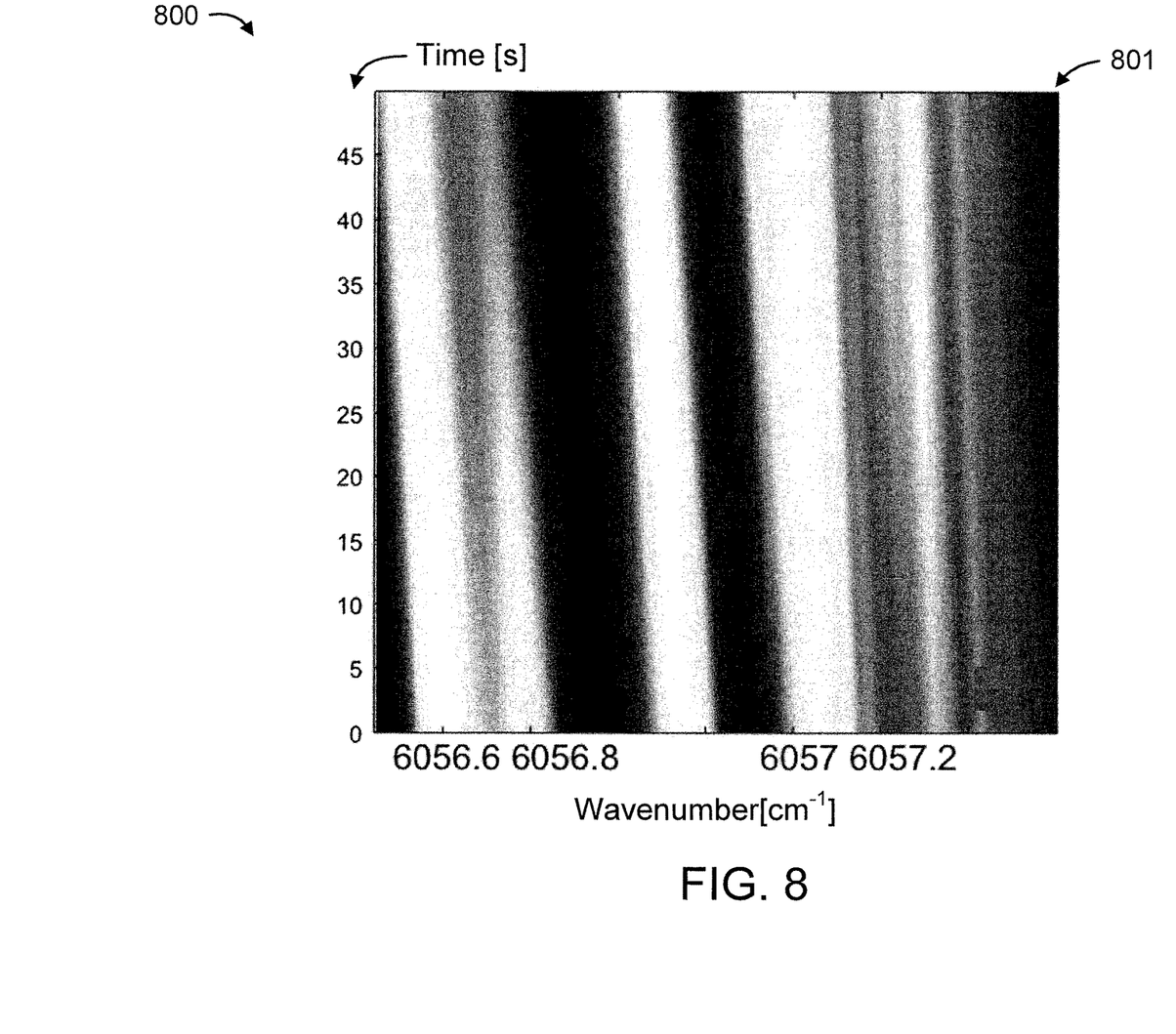
FIG. 8 is a plot showing the uncorrected background spectra, in accordance with an embodiment of the present invention.
Figure 9:
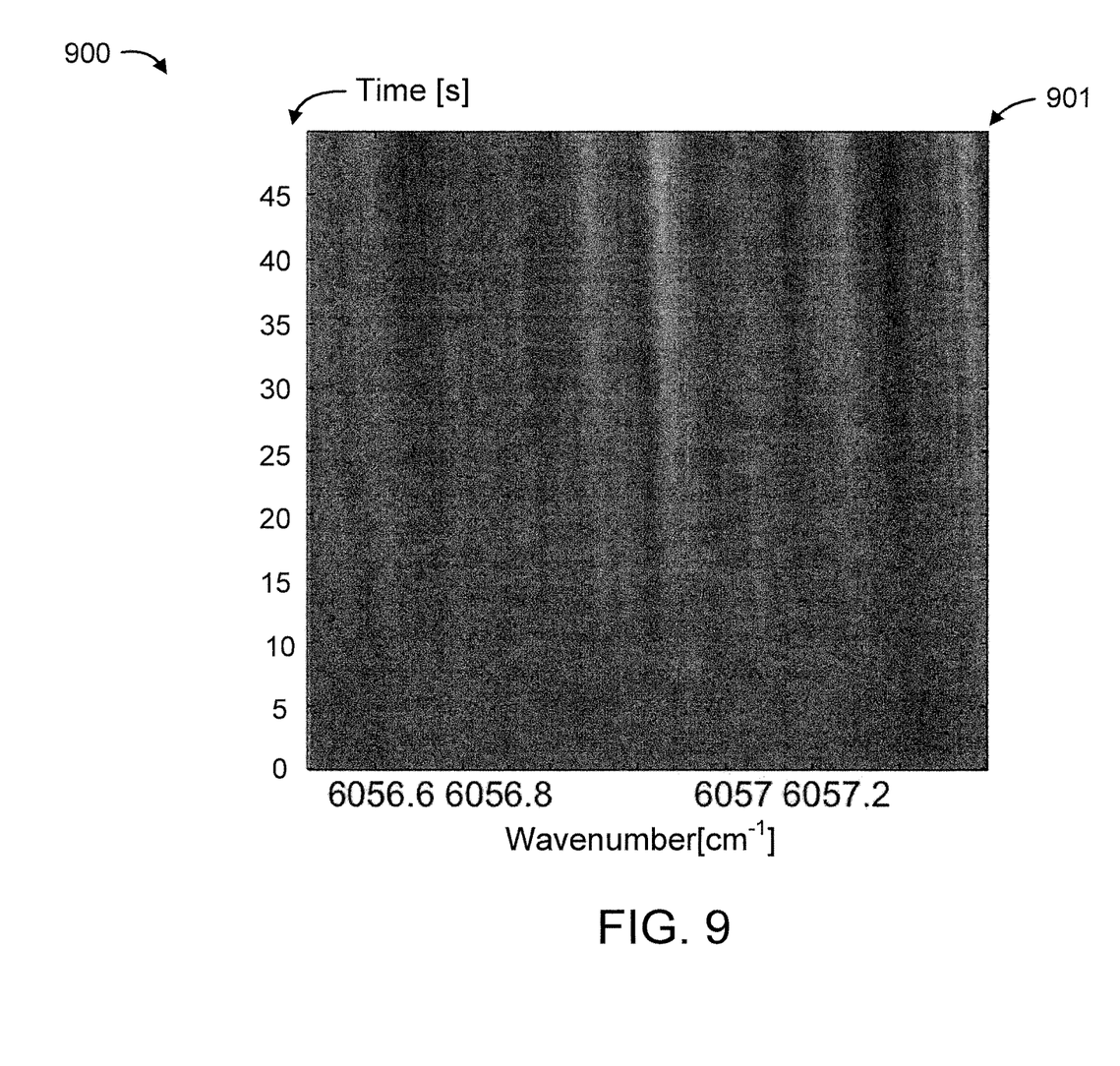
FIG. 9 is a plot showing the corrected spectra using partitioned etalon correction, in accordance with an embodiment of the present invention.

Not only do we obtain significant improvement of signal-to-fringe ratio after the proposed correction, we also experimentally verify that the stability of concentration retrieval is correspondingly improved. FIG. 7 is a plot 799 showing a time series of three zero-gas measurements (701, 702, and 703, respectively) using the same silicon photonic waveguide sensor under the three different scenarios (i.e., concentration retrieval methods 601, 602, and 603, namely uncorrected, uniform background correction, and partitioned etalon correction, respectively) mentioned above, in accordance with an embodiment of the present invention. The plot 799 shows time (in seconds) in the x-axis versus methane concentration (ppmv) in the y-axis. Without etalon correction, sensor stability quickly deteriorates due to fringe drift. FIG. 8 is a plot 801 showing the uncorrected (normalized) background spectra 800, in accordance with an embodiment of the present invention. The plot 801 shows wavenumber (in cm$^{-1}$) in the x-axis versus time (in seconds) in the y-axis. In particular, FIG. 8 shows the time evolution of uncorrected (normalized) spectra 800 throughout the 50 s acquisition duration. However, with uniform background correction, which clearly shows improved signal-to-fringe ratio in FIG. 6, the retrieved concentration as shown in FIG. 7 reveals effects of uncorrected etalon drift. With the zero-gas the retrieved concentration is expected to be zero, but due to etalons in the system there is a visible varying contribution to concentration retrieval error observed as a departure from zero over time for different fringe mitigation techniques. FIG. 7 shows that the best result is observed when the proposed method (i.e., method 200 of FIG. 2) is applied, since the retrieved concentration is maintained around 0 throughout the 50 s duration. FIG. 9 is a plot 901 showing the corrected spectra 900 using partitioned etalon correction, in accordance with an embodiment of the present invention. While some residual etalons are still visible, their amplitudes are significantly reduced. More importantly, the particular choice of etalon partitioning regions here is able to minimize concentration retrieval error despite the many different etalons present in the system.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as SMALLTALK, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Reference in the specification to "one embodiment" or "an embodiment" of the present invention, as well as other variations thereof, means that a particular feature, structure, characteristic, and so forth described in connection with the embodiment is included in at least one embodiment of the present invention. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

Having described preferred embodiments of a system and method (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

What is claimed is:

1. A computer-implemented method for Fourier domain dynamic correction of optical fringes in a laser spectrometer, comprising:
   Fourier transforming, by a processor, a background spectrum contaminated with the optical fringes to obtain baseline fringes in a frequency domain;
   partitioning, by the processor, the baseline fringes in the frequency domain using bandpass filtering to obtain partitioned baseline fringes;
   reconstructing, by the processor, the partitioned baseline fringes as separate spectra using an inverse Fourier transform;
   constructing, by the processor, a fitting model to approximate the background spectrum by assigning a first and a second free parameter to each of partitioned baseline fringe components to respectively allow for drift and amplitude adjustments during a fitting of the fitting model; and
   applying, by the processor, the fitting model to a newly acquired spectrum to provide an interpretation of the newly acquired spectrum having a reduced influence of spectral contamination on concentration retrieval.

2. The computer-implemented method of claim 1, wherein the fitting model uses the Least-Means-Squares (LMS) algorithm to perform spectral fitting.

3. The computer-implemented method of claim 1, further comprising repeating the transforming, partitioning, reconstructing, and constructing steps to obtain updated fringe spectra components responsive to another background spectrum becoming available.

4. The computer-implemented method of claim 1, wherein the fitting model further includes an absorption profile of a gas of interest.

5. The computer-implemented method of claim 1, wherein said reconstructing step reconstructs the partitioned baseline fringes by the inverse Fourier transform of band-pass filtered etalons.

6. The computer-implemented method of claim 5, wherein the fitting model includes correction of each of the partitioned baseline fringe components and a polynomial baseline specific to the laser L-I characteristic.

7. The computer-implemented method of claim 6, wherein the polynomial baseline is determined by acquiring a laser intensity as a function of a laser wavelength.

8. The computer-implemented method of claim 1, further comprising selecting partitioning regions for said partitioning step that minimize an error in approximating the background spectrum.

9. The computer-implemented method of claim 1, wherein the background spectrum contaminated with the optical fringes serves as a baseline spectrum for the correction of the optical fringes.

10. The computer-implemented method of claim 1, wherein the first and the second free parameter are accounted for by the fitting model in order to achieve the dynamic correction of the optical fringes.

11. A computer program product for Fourier domain dynamic correction of optical fringes in a laser spectrometer, the computer program product comprising a non-transitory computer readable storage medium having program instructions embodied therewith, the program instructions executable by a computer to cause the computer to perform a method comprising:
Fourier transforming, by a processor, a background spectrum contaminated with the optical fringes to obtain baseline fringes in a frequency domain;
partitioning, by the processor, the baseline fringes in the frequency domain using bandpass filtering to obtain partitioned baseline fringes;
reconstructing, by the processor, the partitioned baseline fringes as separate spectra using an inverse Fourier transform;
constructing, by the processor, a fitting model to approximate the background spectrum by assigning a first and a second free parameter to each of partitioned baseline fringe components to respectively allow for drift and amplitude adjustments during a fitting of the fitting model; and
applying, by the processor, the fitting model to a newly acquired spectrum to provide an interpretation of the newly acquired spectrum having a reduced influence of spectral contamination on concentration retrieval.

12. The computer program product of claim 11, wherein the fitting model uses the Least-Means-Squares (LMS) algorithm to perform spectral fitting.

13. The computer program product of claim 11, wherein the method further comprises repeating the transforming, partitioning, reconstructing, and constructing steps to obtain updated fringe spectra components responsive to another background spectrum becoming available.

14. The computer program product of claim 11, wherein the fitting model further includes an absorption profile of a gas of interest.

15. The computer program product of claim 11, wherein said reconstructing step reconstructs the partitioned baseline fringes by the inverse Fourier transform of band-pass filtered etalons.

16. The computer program product of claim 14, wherein the fitting model includes correction of each of the partitioned baseline fringe components and a polynomial baseline specific to the laser L-I characteristic.

17. The computer program product of claim 11, wherein the method further comprises selecting partitioning regions for said partitioning step that minimize an error in approximating the background spectrum.

18. The computer program product of claim 11, wherein the partitioned baseline fringes represent etalon features relating to respective smaller effective cavity lengths than the background spectrum contaminated with the optical fringes.

19. The computer program product of claim 11, wherein the first and the second free parameter are accounted for by the fitting model in order to achieve the dynamic correction of the optical fringes.

20. A system for Fourier domain dynamic correction of optical fringes in a laser spectrometer, comprising:
a memory for storing program code; and
a processor, operatively coupled to the memory, for running the program code to:
Fourier transform a background spectrum contaminated with the optical fringes to obtain baseline fringes in a frequency domain;
partition the baseline fringes in the frequency domain using bandpass filtering to obtain partitioned baseline fringes;
reconstruct the partitioned baseline fringes as separate spectra using an inverse Fourier transform;
construct a fitting model to approximate the background spectrum by assigning a first and a second free parameter to each of partitioned baseline fringe components to respectively allow for drift and amplitude adjustments during a fitting of the fitting model; and
apply the fitting model to a newly acquired spectrum to provide an interpretation of the newly acquired spectrum having a reduced influence of spectral contamination on concentration retrieval.

* * * * *